United States Patent [19]

Eidenschink et al.

[11] 4,154,697

[45] May 15, 1979

[54] LIQUID CRYSTALLINE HEXAHYDROTERPHENYL DERIVATIVES

[75] Inventors: Rudolf Eidenschink; Joachim Krause; Ludwig Pohl, all of Darmstadt, Fed. Rep. of Germany

[73] Assignee: Merck Patent Gesellschaft mit beschraenkter Haftung, Darmstadt, Fed. Rep. of Germany

[21] Appl. No.: 868,573

[22] Filed: Jan. 11, 1978

[30] Foreign Application Priority Data

Jan. 15, 1977 [DE] Fed. Rep. of Germany ....... 2701591

[51] Int. Cl.² .................. C07C 121/64; C07C 121/75; C09K 3/34
[52] U.S. Cl. ................. 252/299; 260/465 F; 260/465 R; 260/544 P; 260/558 R; 260/571; 260/590 C; 260/592; 562/469; 562/492; 568/807; 350/350
[58] Field of Search ...................... 260/465 R, 465 F; 252/299; 350/350

[56] References Cited

U.S. PATENT DOCUMENTS

| | | | |
|---|---|---|---|
| 3,947,375 | 3/1976 | Gray et al. | 252/299 |
| 4,013,582 | 3/1977 | Gavrilovic | 252/299 |
| 4,029,594 | 6/1977 | Gavrilovic et al. | 252/299 |
| 4,029,595 | 6/1977 | Ross et al. | 252/299 |

*Primary Examiner*—Dolph H. Torrence
*Attorney, Agent, or Firm*—Millen & White

[57] ABSTRACT

Novel liquid crystals have the formula

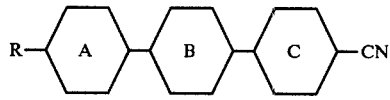

wherein two of the rings A, B and C are aromatic and the third is a trans-1,4-disubstituted cyclohexane ring and R is alkyl or alkoxy each of 1 – 12 C-atoms. These compounds are particularly useful as additional components in liquid crystal dielectrics whereby the clear point of the dielectric is raised and the viscosity thereof is not deleteriously affected.

14 Claims, No Drawings

LIQUID CRYSTALLINE HEXAHYDROTERPHENYL DERIVATIVES

BACKGROUND OF THE INVENTION

The present invention is concerned with liquid crystalline cyclohexane derivatives and with dielectric compositions containing them.

To an increasing extent, the properties of nematic or nematic-cholesteric liquid crystalline materials are being utilized for electro-optical indicating elements. This utility derives from the fact that the optical properties of these materials such as light scattering, birefringence, reflecting power or color, change under the influence of electric fields. The function of such indicator elements thereby depends, for example, upon the phenomenon of dynamic scattering, the deformation of aligned phases, the Schadt-Helfrich effect in the twisted cell or the cholestericnematic phase transition.

For the technical use of these effects in electronic elements, liquid crystalline materials which must satisfy a plurality of requirements are needed. Especially important is a chemical stability to moisture, air and physical influences, such as heat, infra-red, visible and ultraviolet radiation and direct and alternating electric fields. Furthermore, there is required a liquid crystalline mesophase in the temperature range of at least +10° C. to +60° C. and preferably of 0° C. to 60° C., and a low viscosity at ambient temperature, which should preferably be not more than 70 cP. Finally, they should not exhibit an inherent absorption of visible light, i.e., they must be colorless.

A number of liquid crystalline compounds is already known. These satisfy the stability requirements demanded of dielectrics for use in electronic display elements and are also colorless. These include, in particular, the p,p'-disubstituted benzoic acid phenyl esters described in U.S. Patent Specification No. 4,002,670 (German Patent Application No. 2,139,628) and the p,p'-disubstituted biphenyl derivatives described in U.S. Patent Specification No. 3,947,375 (German Patent Application No. 2,356,085). In both of these classes of compounds, as well as in other known series of compounds having a liquid crystalline mesophase, there are no individual compounds which form a liquid crystalline nematic mesophase in the required temperature range of 10° C. to 60° C. Therefore, as a rule, mixtures of two or more compounds are produced in order to obtain materials which can be used as liquid crystalline dielectrics.

For this purpose, it is customary to mix at least one compound having a low melting or clear point with another having a distinctly higher melting and clear point. A mixture is thus normally obtained, the melting point of which is below that of the lower melting component. However, optimal dielectrics cannot be prepared in this way since the components with the high melting and clear points almost always impart a high viscosity to the mixture. Consequently, the switch times of the electro-optical indicator elements produced therewith are thereby prolonged in an undesirable manner.

SUMMARY OF THE INVENTION

It is an object of the present invention to provide liquid crystalline dielectrics which exhibit a nematic phase in the required temperature range and permit short switch times in liquid crystal cells at ambient temperature.

In a composition aspect, this invention relates to novel hexahydroterphenyl derivatives of the general formula (I)

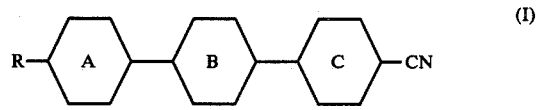

wherein two of the rings A, B and C are aromatic and the third is a trans-1,4-disubstituted cyclohexane ring and R is alkyl or alkoxy each of 1 – 12 C-atoms. In another composition aspect, this invention provides mixtures containing the novel compounds of this invention. These compounds and mixtures are outstandingly useful materials for the production of liquid crystalline dielectrics.

Furthermore, the present invention provides liquid crystalline dielectric compositions containing at least two liquid crystalline components, at least one of which is a hexahydroterphenyl derivative of formula (I).

This invention also provides a liquid crystal display element wherein the dielectric comprises a compound of formula (I).

DETAILED DISCUSSION

Although the compounds of formula (I) in general possess such high melting (over 90° C.) and clear points (over 170° C.) that they individually are normally not suitable for use as dielectrics in electronic indicator elements operated at room temperature, addition of these compounds to other liquid crystalline substances achieves a significant lowering of melting point, as well as an advantageous increase in the clear point. At the same time, they do not cause an undesired increase in viscosity of the mixture.

The hexahydroterphenyl derivatives of formula (I) fall into three classes:

4-(4-trans-R-cyclohexyl)-4'-cyanobiphenyls of formula (II)

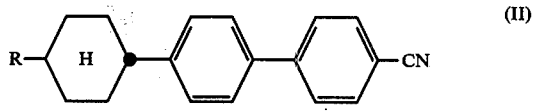

trans-1-(p-R-phenyl)-4-(p-cyanophenyl)-cyclohexanes of formula (III).

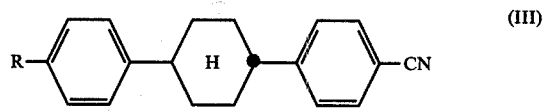

and 4-R-4'-(4-trans-cyanocyclohexyl)-biphenyls of formula (IV)

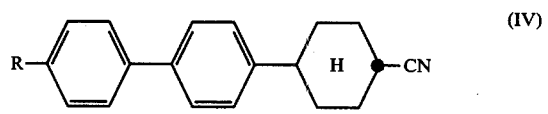

wherein R in the formulae (II), (III) and (IV) is as defined for formula (I).

The hexahydroterphenyl derivatives of formula (I) possess a positive dielectric anisotropy and are, therefore, suitable for use as components of liquid crystalline dielectrics in those indicator elements which function on the basis of the Schadt-Helfrich effect in the twisted nematic cell or which utilize the phenomenon of the cholesteric-nematic phase transition.

Substituent R in the compounds of formula (I) can be straight-chained or branched. When R is straight-chained, it can be methyl, ethyl, n-propyl, n-butyl, n-pentyl, n-hexyl, n-heptyl, n-octyl, n-nonyl, n-decyl, n-undecyl, n-dodecyl or the corresponding alkoxy radicals. Such straight-chained compounds of formula (I) generally possess especially high clear points.

Especially preferred compounds of formula (I) are those in which R is an alkyl radical of 1-10, especially 3-8, or an alkoxy radical of 1-8, especially 3-7, C- atoms.

Compounds of formula (I) having branched R substituents are also included and sometimes are also of high importance since they frequently display better solubility properties in the customary liquid crystalline base mixtures. Such branched R substituents preferably contain not more than one chain branching. Preferred branched R substituents are those in which the carbon atom chain is branched on the binding carbon atom or on one of the two next carbon atoms. Of particular importance among these are those branched groups in which there is in the 1-, 2- or 3-position a methyl or ethyl group, for example, isopropyl, 1-methylpropyl, 2-methylpropyl, 1-methylbutyl, 2-methylbutyl, 3-methylbutyl, 1-methylpentyl, 1-ethylpentyl, 2-methylpentyl, 1-methylhexyl, 2-ethylhexyl or 1-methylheptyl, as well as the corresponding alkoxy groups. Among these, those radicals having a main chain length of from 4 to 6 carbon atoms are preferred.

Generally, when R is a branched chain group, from 4 to 8 total carbon atoms are preferred.

The compounds of formula (I) are prepared in the conventional fashion for such compounds. For example, a compound of formula (V)

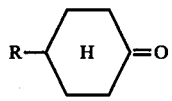

(V)

wherein R is as defined for formula (I), may be reacted with a compound of formula (VI)

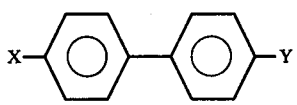

(VI)

wherein X is H or an amino group protected against reaction with organo-metallic reagents by protective groups which are easily split off, for example trimethylsilyl groups, and Y is —Me$^1$ or —Me$^2$—Hal, whereby Me$^1$ and Me$^2$ are metal atoms of Main Groups I or II of the Periodic Table of the Elements, preferably lithium or magnesium, and Hal is halogen, preferably chlorine or bromine. The resultant product is hydrolyzed to a compound of formula (VII)

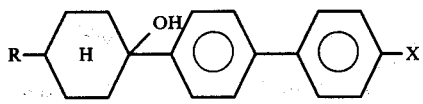

(VII)

After conventional separation of the cis-trans-isomeric alcohols (VII), the separated isomers are individually reduced in fully conventional manner, for example, by catalytic hydrogenation, with inversion or retention of the configuration of the benzylpositioned carbon atoms, to the trans-conformation hexahydroterphenyl derivatives (VIII).

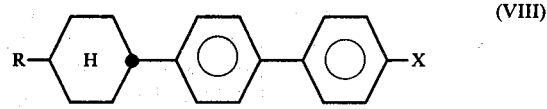

(VIII)

X in these compounds of formula (VIII), is then converted also in fully conventional fashion into a nitrile group. Thus, for example, when X is a hydrogen atom, the compound of formula (VIII) is reacted in the presence of aluminium chloride with acetyl chloride to produce the corresponding acetophenone derivative. This is then oxidized, e.g., with hypohalite or with iodine, to the corresponding benzoic acid (IX)

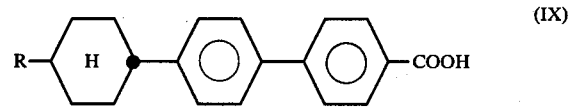

(IX)

The benzoic acid (IX) is then converted in fully conventional fashion into the nitrile (II) by successive treatment with thionyl chloride, ammonia and phosphorus oxychloride, via the intermediates of the corresponding benzoyl chloride and benzamide.

Alternatively, a compound of formula (VIII), in which X is hydrogen, can be conventionally reacted with thallium tristrifluoroacetate to produce the corresponding phenyl thallium-bis-trifluoroacetate. This can then be subjected to conventional UV irradiation in aqueous solution in the presence of potassium cyanide, whereby the nitrile (II) is formed.

Compounds of formula (VIII), in which X is a protected amino group, after conventional removal of the protective group, can be converted into the nitrile (II) by diazotization and subsequent reaction with dicyanocuprate.

The compounds of formula (III) can also be prepared fully analogously to the compounds of formula (II) by first reacting a 4-alkyl-(or alkoxy)-phenyl magnesium bromide with 4-phenylcyclohexanone, followed by hydrolysis of the reaction mixture, thereby obtaining the cis-trans-isomeric 1-(4-alkyl- or alkoxyphenyl)-4-phenyl-cyclohexanols. After separation and hydrogenation with inversion or retention of the configuration, these are converted into trans-4-(4-alkyl- or alkoxyphenyl)-1-phenyl-cyclohexane. The nitrile group is introduced into the 4-position of the unsubstituted phenyl nucleus of these compounds as described above via the corresponding acetophenone derivative or the phenyl thallium bis-trifluoroacetate derivative.

The compounds of formula (IV) may be obtained by reacting cyclohexene with acetyl chloride in the presence of aluminum chloride to produce 4-acetylcyclohexyl chloride. This, in turn, is reacted in the presence of aluminum chloride with a compound of the formula R-(p)—C$_6$H$_4$—C$_6$H$_5$ to give 4—[4—(R)—biphenylyl—(4')]-1-acetylcyclohexane. The acetyl group in this intermediate product is converted into a carboxyl group by oxidation with hypohalite, and the latter group converted via the acid chloride and acid amide into a nitrile group.

All the foregoing chemical reactions involved in the several preparative schemes discussed above are well known and may be conducted using the conventional conditions disclosed in the literature, e.g., in Houben-Weyl, Methoden der Organischen Chemie (Methods of Organic Chemistry), Fourth Edition, Georg-Thieme-Verlag, Stuttgart, Germany.

The starting materials for the preparation of the compounds of this invention are either known or can be readily prepared without difficulty using processes known and described in the literature. Thus, for example, the 4-alkylcyclohexanones (formula V, R = alkyl) can be obtained by catalytically hydrogenating the corresponding 4-alkylphenols. The so-obtained 4-alkylcyclohexanols are then oxidized to the corresponding ketones. The 4-alkoxycyclohexanones can be prepared analogously by hydrogenation of the corresponding hydroquinone hemiethers and subsequent oxidation of the so-obtained 4-alkoxycyclohexanols.

The compounds of formula (I) are valuable components for use in liquid crystalline dielectrics suitable for the production of electro-optical indicator elements.

The dielectrics of this invention consist of two or more components, including at least one of formula (I). The additional components are preferably nematic or nematogenic. Suitable classes of such compounds include the azobenzenes, azoxybenzenes, biphenyls, Schiff bases, especially benzylidene derivatives, phenyl benzoates, phenyl cyclohexanes, optionally halogenated stilbenes, diphenylacetylene derivatives, diphenyl nitrones and substituted cinnamic acids. The most important compounds for use as such additional components have the formula (X):

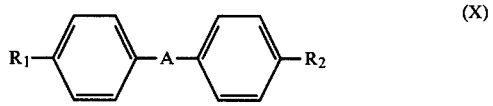

wherein

A is

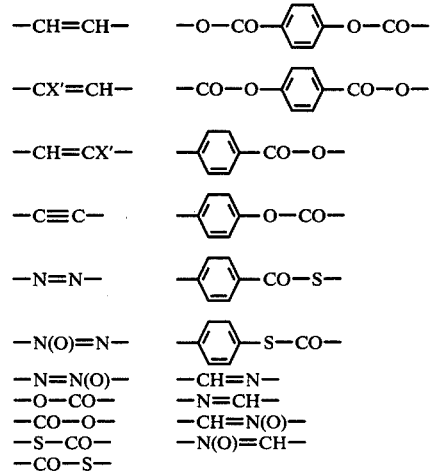

or a C—C single bond. When A is —CO—O—, —O—CO— or a C—C single bond, one of the two phenyl rings can be replaced by a trans-cyclohexyl ring. X' is halogen, preferably Cl. $R_1$ and $R_2$ may be the same or different and ech is alkyl, alkoxy, alkanoyl, alkanoyloxy or alkoxycarbonyloxy radicals of up to 18, preferably up to 8 C-atoms. Furthermore, one of $R_1$ and $R_2$ can also be a cyano-, nitro or isonitrile group. In the case of most of these compounds, $R_1$ and $R_2$ are preferably different, whereby one of the radicals very usually is an alkyl or alkoxy group. However, a large number of other variant combinations of the permissible substituents are also conventional. Many such nematic substances are commercially available.

The dielectrics of this invention contain up to 30, normally 1–20, preferably 5–14 parts by weight, based on the total weight of the liquid-crystalline dielectric, of one or more of the compounds of the formula (I).

By addition of the compounds of formula (I), independent of the nature and composition of the liquid crystalline base substance increases of the clear point of 5–40 degrees Centigrade are achieved. At the same time, the viscosity of the base substance, and thus the switch time of indicator elements using the resultant dielectrics, is not deleteriously affected.

By inclusion of suitable additives, the liquid crystalline dielectrics of this invention can be modified so that they can be employed in all previously known types of indicator elements which use liquid crystal having positive dielectric anisotropy. Such additives are conventional and are known to the skilled artisan. They are described in detail in the relevant literature. For example, conventional additives exist for changing the dielectric anisotropy and/or the orientation of the nematic phases. Substances of this type are described, for example, in laid-open German Patent Applications P 22 09 127, P 23 21 632 and P 26 11 453.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the Examples, m.p. is the melting point and c.p. the clear point of a liquid crystalline substance in degrees Celsius. Boiling temperatures are indicated by b.p. Unless otherwise noted, statements of parts or percentages refer to parts by weight or percentages by weight. All viscosities are measured at 20°.

EXAMPLE 1

(a) To a solution of biphenyl magnesium bromide prepared from 46.6 g of 4-bromobiphenyl, and 4.9 g of magnesium turnings in 250 ml of diethyl ether, there is added dropwise with stirring and cooling, over the course of one hour, a solution of 34.0 g of 4-n-pentylcyclohexanone in 100 ml of diethyl ether. The reaction mixture is further heated to the boil for 1 hour and then poured into a solution of 20 ml of concentrated hydrochloric acid in 400 ml of ice water. The ether phase is separated off and the aqueous phase shaken out twice with 100 ml of diethyl ether. The combined ether phases are washed with 5% sodium hydrogen carbonate solution and then with water, dried over sodium sulphate and evaporated. The residue is subjected to a separation on a column filled with silica gel. The 1-biphenylyl-cis-4-n-pentyl-r-cyclohexanol eluted with petroleum ether (boiling range 40°–60°) is dissolved in 500 ml of ethanol and hydrogenated in the presence of 25 g of moist Raney nickel at normal pressure for 72 hours. The trans compound, which is eluted with a mixture of petroleum ether (40°–60°) and diethyl ether (15 volume percent), is dissolved in 500 ml of ethanol and hydrogenated in the presence of 8 g of palladium charcoal (5% Pd) at normal pressure for 48 hours. After filtering off the catalyst, the alcoholic solutions are combined and evaporated. The 4-[trans-(4-n-pentyl)-cyclohexyl]-biphenyl obtained in oily form is further worked-up without purification.

(b) A suspension of 14.6 g of aluminum chloride in 100 ml of dichloromethane is successively mixed, with ice cooling, with 8.6 g of acetyl chloride and a solution of 33.7 g of 4-[trans-(4-n-pentyl)-cyclohexyl]-biphenyl in 100 ml of dichloromethane. The reaction mixture is further stirred for 2 hours, poured onto 300 g of ice and mixed with sufficient concentrated hydrochloric acid that the precipitated aluminum hydroxide is dissolved. The organic phase is separated off and the aqueous phase washed twice with 100 ml amounts of dichloromethane. The combined organic phases are dried over calcium chloride and evaporated. The 4-acetyl-4'-[trans-(4-n-pentyl)-cyclohexyl]-biphenyl left behind is recrystallised from ethanol; m.p. 125°, c.p. 200°.

(c) 14.0 g of 4-acetyl-4'-[trans-(4-n-pentyl)-cyclohexyl]-biphenyl are heated, together with 30 g of iodine and 100 ml of pyridine on a steambath for 2 hours. After the pyridine is evaporated off under reduced pressure, the residue is dissolved in chloroform and purified over a short silica gel column. The eluate is evaporated and the 4'-[trans-(4-n-pentyl)-cyclohexyl]-4-biphenylcarboxylic acid left behind is heated to the boil for 2.5 hours with 30 ml of thionyl chloride. After distilling off the excess thionyl chloride, the 4'-[trans-(4-n-pentyl)-cyclohexyl]-4-biphenylcarboxylic acid chloride is dissolved in 250 ml of dioxane and this solution mixed with 100 ml of 25% aqueous ammonia solution. The reaction mixture is poured into 1.5 liters of ice water and the precipitated 4'-[trans-(4-n-pentyl)-cyclohexyl]-4-biphenyl-carboxylic acid amide filtered off and dried. The dried amide is dissolved at 40° in 170 ml of dimethyl formamide. To this solution are added dropwise at 50°, in the course of 30 minutes, 26 g of phosphorus oxide trichloride. After 1 hour, the reaction mixture is poured into 300 ml of ice water. By several extractions with 100 ml amounts of dichloromethane, washing of the extracts with 5% sodium bicarbonate solution and then with water, drying over sodium sulphate and evaporation, 4-cyano-4'-(trans-4-pentyl-cyclohexyl)-biphenyl is isolated. It is purified by recrystallisation from ethanol; m.p. 93°, c.p. 219°.

There are prepared analogously:
4-cyano-4'-(trans-4-methylcyclohexyl)-biphenyl, m.p. 151°, c.p. 186°;
4-cyano-4'-(trans-4-ethylcyclohexyl)-biphenyl.
4-cyano-4'-(trans-4-n-propylcyclohexyl)-biphenyl, m.p. 132°, c.p. 230°;
4-cyano-4'-(trans-4-isopropylcyclohexyl)-biphenyl,
4-cyano-4'-(trans-4-n-butylcyclohexyl)-biphenyl,
4-cyano-4'-[trans-4-(1-methylpropyl)-cyclohexyl]-biphenyl,
4-cyano-4'-[trans-4-(2-methylpropyl)-cyclohexyl]-biphenyl,
4-cyano-4'-[trans-4-(1-methylbutyl)-cyclohexyl]-biphenyl,
4-cyano-4'-[trans-4-(2-methylbutyl)-cyclohexyl]-biphenyl,
4-cyano-4'-[trans-4-(3-methylbutyl)-cyclohexyl]-biphenyl,
4-cyano-4'-(trans-4-n-hexylcyclohexyl)-biphenyl,
4-cyano-4'-[trans-4-(1-methylpentyl)-cyclohexyl]-biphenyl,
4-cyano-4'-[trans-4-(2-methylpentyl)-cyclohexyl]-biphenyl,
4-cyano-4'-[trans-4-n-heptylcyclohexyl)-biphenyl, m.p. 77°, c.p. 206°;
4-cyano-4'-[trans-4-(1-methylhexyl)-cyclohexyl]-biphenyl,
4-cyano-4'-[trans-4-(1-ethylpentyl)-cyclohexyl]-biphenyl,
4-cyano-4'-(trans-4-n-octylcyclohexyl)-biphenyl, m.p. 61°, c.p. 188°;
4-cyano-4'-[trans-4-(1-methylheptyl)-cyclohexyl]-biphenyl,
4-cyano-4'-[trans-4-(2-ethylhexyl)-cyclohexyl]-biphenyl,
4-cyano-4'-(trans-4-n-nonycyclohexyl)-biphenyl, m.p. 63°, c.p. 192°;
4-cyano-4'-(trans-4-n-decylcyclohexyl)-biphenyl,
4-cyano-4'-(trans-4-n-undecylcyclohexyl)-biphenyl, and
4-cyano-4'-(trans-4-n-dodecylcyclohexyl)-biphenyl.

EXAMPLE 2

(a) To a solution of ethyl magnesium bromide prepared from 45.0 g of ethyl bromide and 9.6 g of magnesium turnings in 400 ml of diethyl ether, thee is added dropwise a solution of 49.6 g of 4-amino-4'-bromobiphenyl in 150 ml of diethyl ether. Subsequently, there are added at room temperature 43.2 g of trimethylsilyl chloride in 200 ml of diethyl ether. After heating under reflux for 1 hour, the solvent is evaporated off and the residue is extracted with petroleum benzine (boiling range 60°–80°). From the extract, there are obtained by crystallisation 42.0 g of 4-N,N-bis(trimethylsilyl)-amino-4'-bromobiphenyl. This is dissolved in 200 ml of diethyl ether and mixed at 0° with 54 ml of 2 molar butyl lithium solution in hexane. After stirring for 30 minutes, a solution of 18.2 g of 4-n-butyloxycyclohexanone in 50 ml of diethyl ether is added dropwise thereto. The mixture is heated to the boil for 1 hour and, after cooling to room temperature, stirred with 200 ml of 1N aqueous hydrochloric acid. The organic phase is washed with 100 ml of 5% sodium bicarbonate solution and then with 100 ml of water, dried with sodium sulphate and, after removal of the solvent, analogously to Example 1(a), the residue is separated on a silica gel column, into 1-(4-amino-4'-biphenylyl)-cis-4-n-butyloxy-r-cyclohexanol and 1-(4-amino-4'-biphenylyl)-trans-4-n-butyloxy-4-cyclohexanol. The isomers are hydrogenated analogously to Example 1(a) in the presence of Raney nickel or of palladium charcoal.

(b) A solution of 24 g of 4-amino-4'-(trans-4-n-butyloxycyclohexyl)-biphenyl, obtained in the hydrogenation, in 40 ml of semi-concentrated hydrochloric acid is slowly mixed at 0°, with stirring, with a solution of 5.6 g of sodium nitrite in 35 ml of water. The diazonium salt solution obtained is covered with 150 ml of toluene and, while stirring, slowly mixed with 90 ml of a sodium dicyanocuprate solution prepared from 25 g of copper sulphate pentahydrate and 21 g of sodium cyanide in 100 ml of water. The reaction mixture is further stirred vigorously for 30 minutes at about 80°. Subsequently, the toluene phase is separated off, washed twice with 50 ml amounts of water, dried over sodium sulphate and evaporated. The 4-cyano-4'-(trans-4-n- butyloxycyclohexyl)-biphenyl remaining behind is recrystallised from ethanol.

There are prepared analogously:
4-cyano-4'-(trans-4-methoxycyclohexyl)-biphenyl,
4-cyano-4'-(trans-4-ethoxycyclohexyl)biphenyl,
4-cyano-4'-(trans-4-n-propyloxycyclohexyl)-biphenyl,
4-cyano-4'-(trans-4-isopropyloxycyclohexy)-biphenyl,
4-cyano-4'-[trans-4-(1-methylpropyloxy)-cyclohexyl]-biphenyl,
4-cyano-4'-[trans-4-(2-methylpropyloxy)-cyclohexyl]-biphenyl,
4-cyano-4'-(trans-4-n-pentyloxycyclohexyl)-biphenyl,
4-cyano-4'-[trans-4-(1-methylbutyloxy)-cyclohexyl]-biphenyl,
4-cyano-4'-[trans-4-(2-methylbutyloxy)-cyclohexyl]-biphenyl,
4-cyano-4'-[trans-4-(3-methylbutyloxy)-cyclohexyl]-biphenyl,
4-cyano-4'-(trans-4-n-hexyloxycyclohexyl)-biphenyl,
4-cyano-4'-[trans-4-(1-methylpentyloxy)-cyclohexyl]-biphenyl,
4-cyano-4'-[trans-4-(2-methylpentyloxy)-cyclohexyl]-biphenyl,
4-cyano-4'-(trans-4-n-heptyloxycyclohexyl)-biphenyl,
4-cyano-4'-[trans-4-(1-methylhexyloxy)-cyclohexyl]-biphenyl,
4-cyano-4'-(trans-4-n-octyloxycyclohexyl)-biphenyl,
4-cyano-4'-[trans-4-(1-methylheptyloxy)-cyclohexyl]-biphenyl,
4-cyano-4'-[trans-4-(2-ethylhexyloxy)-cyclohexyl]-biphenyl,
4-cyano-4'-(trans-4-n-nonyloxycyclohexyl)-biphenyl, and
4-cyano-4'-(trans-4-n-decyloxycyclohexyl)-biphenyl.

EXAMPLE 3

(a) To a solution of 4-n-pentylphenyl magnesium bromide prepared from 45.5 g of 4-n-pentylbromobenzene and 4.9 g of magnesium turnings in 250 ml of diethyl ether there is added dropwise, with stirring and cooling, a solution of 34.8 g of 4-phenylcyclohexanone in 100 ml of diethyl ether. The reaction mixture is further heated to the boil for 1 hour and then poured into a solution of 20 ml of concentrated hydrochloric acid in 400 ml of ice water. The ether phase is separated off and the aqueous phase further shaken out twice with 100 ml of diethyl ether. The combined ether phases are washed with 5% sodium hydrogen carbonate solution and then with water, dried over sodium sulphate and evaporated. The residue is subjected to a separation via a column filled with silica gel. As elution agents, petroleum ether (40°–60°) is first used and then petroleum ether/diethyl ether mixtures with a proportion of diethyl ether increasing from 2 to 15 vol.%. There are obtained about equal amounts of 1-(4-n-pentylphenyl)-cis-4-phenyl-r-cyclohexanol and 1-(4-n-pentylphenyl)-trans-4-phenyl-r-cyclohexanol in oily form. The cis compound is dissolved in 500 ml of ethanol and hydrogenated in the presence of 25 g of moist Raney nickel at normal pressure for 72 hours. The trans compound is dissolved in 500 ml of ethanol and also hydrogenated for 48 hours in the presence of 8 g of palladium charcoal (5% Pd). After the filtering off of the catalysts, the alcoholic solutions are combined and evaporated. The trans-4-(4-n-pentylphenyl)-1-phenyl-cyclohexane obtained in oily form is further worked-up without purification.

(b) A suspension of 14.6 g of aluminium chloride in 100 ml of dichloromethane is successively mixed, with ice cooling, with 8.6 g of acetyl chloride and a solution of 33.7 g of trans-(4-(4-n-pentylphenyl)-1-phenylcyclohexane in 100 ml of dichloromethane. The reaction mixture is further stirred for 2 hours, poured onto 300 g of ice and mixed with sufficient concentrated hydrochloric acid that the precipitated aluminum hydroxide is dissolved. The organic phase is separated off and the aqueous phase washed twice with 100 ml amounts of dichloromethane. The combined organic phases are dried over calcium chloride and evaporated. The trans-4-(4-n-pentylphenyl)-1-(4-acetylphenyl)-cyclohexane remaining behind is recrystallised from ethanol.

(c) 14.0 g of trans-4-(4-n-pentylphenyl)-1-(4-acetylphenyl)-cyclohexane are heated for 2 hours on a steam-bath, together with 30 g of iodine and 100 ml of pyridine. After the evaporation of the pyridine under reduced pressure, the residue is dissolved in chloroform and purified over a short silica gel column. The eluate is evaporated and the 4-[trans-4-(4-n-pentylphenyl)-cyclohexyl]-benzoic acid remaining behind is brought to the boil for 2.5 hours with 30 ml of thionyl chloride. After distilling off the excess thionyl chloride, the 4-[trans-4-(4-n-pentylphenyl)-cyclohexyl]-benzoyl chloride is dissolved in 250 ml of dioxane and this solution mixed with 100 ml of 25% aqueous ammonia solution. The reaction mixture is poured into 1.5 liters of ice water and the precipitated 4-[trans-4-(4-n-pentylphenyl)-cyclohexyl]-benzamide filtered off and dried. The dry amide is dissolved at 40° in 170 ml of dimethyl formamide. To this solution are added dropwise at 50°, in the course of 30 minutes, 26 g of phosphorus oxide trichloride. After 1 hour the reaction mixture is poured into 300 ml of icewater. After extracting several times with 100 ml amounts of dichloromethane, washing of the extracts with 5% sodium bicarbonate solution and then with water, drying over sodium sulphate and evaporation, there is obtained trans-4-(4-n-pentylphenyl)-1-(4-cyanophenyl)-cyclohexane which is purified by recrystallisation from ethanol; m.p. 80°, c.p. 160°.

There are obtained analogously:
trans-4-(4-methylphenyl)-1-(4-cyanophenyl)-cyclohexane,
trans-4-(4-ethylphenyl)-1-(4-cyanophenyl)-cyclohexane,
trans-4-(4-n-propylphenyl)-1-(4-cyanophenyl)-cyclohexane,
trans-4-(4-isopropylphenyl)-1-(4-cyanophenyl)-cyclohexane,
trans-4-(4-n-butylphenyl)-1-(4-cyanophenyl)-cyclohexane,
trans-4-[4-(1-methylpropyl)-phenyl]-1-(4-cyanophenyl)-cyclohexane,
trans-4-[2-(2-methylpropyl)-phenyl]-1-(4-cyanophenyl)-cyclohexane,
trans-4-[4-(1-methylbutyl)-phenyl]-1-(4-cyanophenyl)-cyclohexane,
trans-4-[4-(2-methylbutyl)-phenyl]-1-(4-cyanophenyl)-cyclohexane,
trans-4-[4-(3-methylbutyl)-phenyl]-1-(4-cyanophenyl)-cyclohexane,
trans-4-(4-n-hexylphenyl)-1-(4-cyanophenyl)-cyclohexane,
trans-4-[4-(1-methylpentyl)-phenyl]-1-(4-cyanophenyl)-cyclohexane, trans-4-[4-(2-methylpentyl)-phenyl]-1-(4-cyanophenyl)-cyclohexane,
trans-4-(4-n-heptylphenyl)-1-(4-cyanophenyl)-cyclohexane,
trans-4-[4-(1-methylhexyl)-phenyl]-1-(4-cyanophenyl)-cyclohexane,
trans-4-(4-n-octylphenyl)-1-(4-cyanophenyl)-cyclohexane,
trans-4-[4-(1-methylheptyl)-phenyl]-1-(4-cyanophenyl)-cyclohexane,
trans-4-[4-(2-ethylhexyl)-phenyl]-1-(4-cyanophenyl)-cyclohexane,
trans-4-(4-n-nonylphenyl)-1-(4-cyanophenyl)-cyclohexane,
trans-4-(4-n-decylphenyl)-1-(4-cyanophenyl)-cyclohexane,
trans-4-(4-n-undecylphenyl)-1-(4-cyanophenyl)-cyclohexane,
trans-4-(4-n-dodecylphenyl)-1-(4-cyanophenyl)-cyclohexane,
trans-4-(4-methoxyphenyl)-1-(4-cyanophenyl)-cyclohexane,
trans-4-(4-ethoxyphenyl)-1-(4-cyanophenyl)-cyclohexane,
trans-4-(4-n-propyloxyphenyl)-1-(4-cyanophenyl)-cyclohexane,
trans-4-(4-isopropyloxyphenyl)-1-(4-cyanophenyl)-cyclohexane,
trans-4-(4-n-butyloxyphenyl)-1-(4-cyanophenyl)-cyclohexane,
trans-4-[4-(1-methylpropyloxy)-phenyl]-1-(4-cyanophenyl)-cyclohexane,
trans-4-[4-(2-methylpropyloxy)-phenyl]-1-(4-cyanophenyl)-cyclohexane,
trans-4-(4-n-pentyloxyphenyl)-1-(4-cyanophenyl)-cyclohexane,
trans-4-[4-(1-methylbutyloxy)-phenyl]-1-(4-cyanophenyl)-cyclohexane,
trans-4-[4-(2-methylbutyloxy)-phenyl]-1-(4-cyanophenyl)-cyclohexane,
trans-4-[4-(3-methylbutyloxy)-phenyl]-1-(4-cyanophenyl)-cyclohexane,
trans-4-(4-n-hexyloxyphenyl)-1-(4-cyanophenyl)-cyclohexane,
trans-4-[4-(1-methylpentyloxy)-phenyl]-1-(4-cyanophenyl)-cyclohexane,
trans-4-[4-(2-methylpentyloxy)-phenyl]-1-(4-cyanophenyl)-cyclohexane,
trans-4-(4-n-heptyloxyphenyl)-1-(4-cyanophenyl)-cyclohexane,
trans-4-[4-(1-methylhexyloxy)-phenyl]-1-(4-cyanophenyl)-cyclohexane,
trans-4-(4-n-octyloxyphenyl)-1-(4-cyanophenyl)-cyclohexane,
trans-4-[4-(1-methylheptyloxy)-phenyl]-1-(4-cyanophenyl)-cyclohexane,
trans-4-[4-(2-ethylhexyloxy)-phenyl]-1-(4-cyanophenyl)-cyclohexane,
trans-4-(4-n-nonyloxyphenyl)-1-(4-cyanophenyl)-cyclohexane, and
trans-4-(4-n-decyloxyphenyl)-1-(4-cyanophenyl)-cyclohexane.

EXAMPLE 4

(a) To a suspension of 66.6 g of anhydrous aluminum chloride in 200 ml of carbon disulphide there are added at −15°, with stirring, 39 g of acetyl chloride and thereafter 41 g of cyclohexene. The reaction mixture is stirred for 30 minutes at −15° and then the upper carbon disulphide layer is removed and replaced by 400 ml of a solution of 105 g of 4-n-butylbiphenyl in carbon disulphide. After the addition of a further 33.3 g of aluminum chloride, it is warmed, with stirring, to room temperature and further stirred until the end of the HCl evolution. Thereafter, it is poured onto water, the separated aluminum hydroxide is brought into solution with hydrochloric acid, and the organic phase is separated off, dried and distilled. After the stripping off of the solvent, there remains 4-acetyl-1-[4′-n-butylbiphenylyl-(4)]-cyclohexane as yellowish, wax-like product; yield 64 g.

(b) Analogously to Example 1 (c), from 50 g of 4-acetyl-1-[′-n-butylbiphenylyl-(4)]-cyclohexane, there are obtained, by successive reaction with iodine/pyridine, thionyl chloride, ammonia solution and phosphorus oxide trichloride, 21,8 g of 4-cyano-1-[4′-n-butylbiphenylyl-(4)]-cyclohexane.

There are prepared analogously:
4-cyano-1-[4′-methylbiphenylyl-(4)]-cyclohexane,
4-cyano-1-[4′-ethylbiphenylyl-(4)]-cyclohexane,
4-cyano-1-[4′-n-propylbiphenylyl-(4)]-cyclohexane,
4-cyano-1-[4′-n-pentylbiphenylyl-(4)]-cyclohexane,
4-cyano-1-[4′-n-hexylbiphenylyl-(4)]-cyclohexane,
4-cyano-1-[4′-n-heptylbiphenylyl-(4)]-cyclohexane,
4-cyano-1-[4′-n-octylbiphenylyl-(4)]-cyclohexane,
4-cyano-1-[4′-methoxybiphenylyl-(4)]-cyclohexane,
4-cyano-1-[4′-ethoxybiphenylyl-(4)]-cyclohexane,
4-cyano-1-[4′-n-propyloxybiphenylyl-(4)]-cyclohexane,
4-cyano-1-[4′-n-butyloxybiphenylyl-(4)]-cyclohexane,
4-cyano-1-[4′-n-pentyloxybiphenylyl-(4)]-cyclohexane,
4-cyano-1-[4′-n-hexyloxybiphenylyl-(4)]-cyclohexane, and
4-cyano-1-[4′-n-heptyloxybiphenylyl-(4)]-cyclohexane.

The following Examples concern the liquid crystalline dielectrics of this invention:

EXAMPLE 5

A mixture of 41% trans-4-(4-cyanophenyl)-1-n-propylcyclohexane, 35% trans-4-(4-cyanophenyl)-1-n-pentyl-cyclohexane and 24% trans-4-(4-cyanophenyl)-1-n-heptylcyclohexane (prepared analogously to Example 1 from phenyl megnesium bromide and the corresponding 4-n-alkyl-cyclohexanones) has a clear point of 52° and a viscosity of 21 cP at 20°. After the addition of 12% (referred to the weight of the base mixture) of 4-cyano-4′-(trans-4-n-pentyl-cyclohexyl)-biphenyl, the dielectric has a clear point of 72° and a viscosity of 29 cP.

EXAMPLE 6

A mixture of 37% of 4-n-pentyl-4′-cyanobiphenyl, 43% 4-n-heptyl-4′-cyanobiphenyl, as well as 10% each of 4-n-pentyloxy-4′-cyanobiphenyl and 4-n-heptyloxy-4′-cyano-biphenyl, has a clear point of 45° (35 cP). By the addition of 18% (referred to the weight of the base mixture) of trans-4-(4-n-pentylphenyl)-1-(4-cyanophenyl)-cyclohexane, the clear point increases to 66°, whereas the viscosity remains practically unchanged (37 cP).

EXAMPLE 7

A mixture of 67% anisic acid 4-n-pentylphenyl ester and 33% 4-n-hexyloxybenzoic acid 4'-n-pentylphenyl ester has a clear point of 49° and a viscosity of 59 cP. By the addition of 21.5% 4-cyano-4'-(trans-4-n-heptylcyclohexyl)-biphenyl, a mixture is obtained which possesses a clear point of 83° and a viscosity of 50 cP.

EXAMPLE 8

A mixture of 40% 4-n-butyl-4'-methoxyazoxybenzene, 22% 4-ethyl-4'-methoxyazoxybenzene, 20% dimethylaminobenzonitrile and 18% 4-(4-n-butylbenzoyloxy)-benzoic acid 4'-n-butylphenyl ester has a clear point of 31° and a viscosity of 50 cP. By the addition of 15% trans-4-(4-n-hexyloxyphenyl)-1-(4-cyanophenyl)-cyclohexane, the clear point increases to 57°, whereas the viscosity decreased to 45 cP.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hexahydroterphenyl compound of the formula

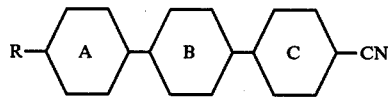

wherein two of the rings A, B and C are aromatic and the third is a trans-1,4-disubstituted cyclohexane ring and R is alkyl or alkoxy each of 1–12 C atoms.

2. The hexahydroterphenyl compound of claim 1 having the formula

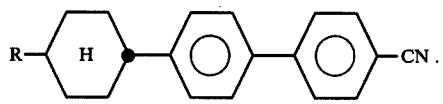

3. The hexahydroterphenyl compound of claim 1 having the formula

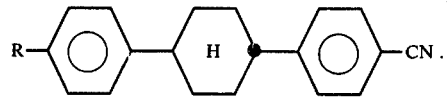

4. The hexahydroterphenyl compound of claim 1 having the formula

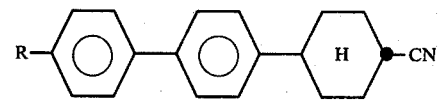

5. The hexahydroterphenyl compound of claim 1 wherein R is an unbranched alkyl or alkoxy.

6. The hexahydroterphenyl compound of claim 1 wherein R is alkyl of 1–10 C atoms.

7. The hexahydroterphenyl compound of claim 1 wherein R is alkoxy of 1–8 C atoms.

8. 4-cyano-4'-(trans-4-n-propylcyclohexyl)-biphenyl, 4-cyano-4'-(trans-4-n-butylcyclohexyl)-biphenyl, 4-cyano-4'-(trans-4-n-pentylcyclohexyl)-biphenyl, 4-cyano-4'-(trans-4-n-hexylcyclohexyl)-biphenyl, 4-cyano-4'-(trans-4-n-heptylcyclohexyl)-biphenyl and 4-cyano-4'-(trans-4-n-octylcyclohexyl)-biphenyl, each a compound of claim 1.

9. 4-cyano-4'-(trans-4-methoxycyclohexyl)-biphenyl, 4-cyano-4'-(trans-4-ethoxycyclohexyl)-biphenyl, 4-cyano-4'-(trans-4-n-propyloxycyclohexyl)-biphenyl, 4-cyano-4'-(trans-4-n-butyloxycyclohexyl)-biphenyl, 4-cyano-4'-(trans-4-n-pentyloxycyclohexyl)-biphenyl, 4-cyano-4'-(trans-4-n-hexyloxycyclohexyl)-biphenyl, 4-cyano-4'-(trans-4-n-heptyloxycyclohexyl)-biphenyl, 4-cyano-4'-(trans-4-n-octyloxycyclohexyl)-biphenyl, 4-cyano-4'-[trans-4-(2-methylbutyloxy)-cyclohexyl]-biphenyl and 4-cyano-4'-[trans-4-(2-ethylhexyloxy)-cyclohexyl]-biphenyl, each a compound of claim 1.

10. Trans-4-(4-n-propylphenyl)-1-(4-cyanophenyl)-cyclohexane, trans-4-(4-n-butylphenyl)-1-(4-cyanophenyl)-cyclohexane, trans-4-(4-n-pentylphenyl)-1-(4-cyanophenyl)-cyclohexane, trans-4-(4-n-hexylphenyl)-1-(4-cyanophenyl)-cyclohexane, trans-4-(4-n-heptylphenyl)-1-(4-cyanophenyl)-cyclohexane and trans-4-(4-n-octylphenyl)-1-(4-cyanophenyl)-cyclohexane, each a compound of claim 1.

11. A liquid crystalline dielectric composition having at least 2 liquid crystalline components, wherein at least one component is a hexahydroterphenyl compound of claim 1.

12. The composition of claim 11 wherein at least one component is not a hexahydroterphenyl compound of claim 1.

13. The liquid crystalline dielectric composition of claim 11, wherein the amount of hexahydroterphenyl compound is up to 30 percent by weight.

14. A liquid crystalline display element whose dielectric comprises a hexahydroterphenyl compound of claim 1.

* * * * *